(12) United States Patent
Rhodes

(10) Patent No.: US 9,448,177 B2
(45) Date of Patent: Sep. 20, 2016

(54) FLAME PHOTOMETRIC DETECTOR

(71) Applicant: AGILENT TECHNOLOGIES, INC., Loveland, CO (US)

(72) Inventor: Robert P. Rhodes, Lincoln University, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 63 days.

(21) Appl. No.: 13/660,273

(22) Filed: Oct. 25, 2012

(65) Prior Publication Data

US 2014/0118742 A1 May 1, 2014

(51) Int. Cl.
*G01N 30/68* (2006.01)
*G01N 21/72* (2006.01)
*H05B 3/40* (2006.01)
*H05B 1/02* (2006.01)

(52) U.S. Cl.
CPC ............. *G01N 21/72* (2013.01); *G01N 30/68* (2013.01); *H05B 1/0247* (2013.01); *H05B 3/40* (2013.01)

(58) Field of Classification Search
CPC .. G01N 31/12; G01N 21/76; G01N 33/0014; G01N 33/0042; G01N 33/203; G01N 33/287
USPC ............... 422/82.01, 54, 83, 91, 94
See application file for complete search history.

(56) References Cited

U.S. PATENT DOCUMENTS

| 3,879,126 | A | * | 4/1975 | Delew ......................... 356/315 |
| 4,018,562 | A | | 4/1977 | Parks et al. |
| 4,269,804 | A | | 5/1981 | Kring |
| 4,352,779 | A | | 10/1982 | Parks |
| 5,227,135 | A | | 7/1993 | Godec et al. |
| 5,614,417 | A | | 3/1997 | Kubala et al. |
| 5,728,586 | A | | 3/1998 | Platzer |
| 5,739,038 | A | | 4/1998 | Burrows |
| 5,786,887 | A | | 7/1998 | Ebata et al. |
| 6,093,371 | A | * | 7/2000 | Wilson ........................... 422/89 |
| 6,143,245 | A | | 11/2000 | Yan et al. |
| 6,205,841 | B1 | * | 3/2001 | Shibamoto .................. 73/23.41 |
| 6,444,326 | B1 | | 9/2002 | Smith |
| 6,580,067 | B1 | | 6/2003 | Yamada et al. |
| 6,723,286 | B2 | | 4/2004 | Sakairi et al. |
| 7,744,818 | B2 | | 6/2010 | Iwamoto et al. |
| 7,906,071 | B2 | | 3/2011 | Warchol et al. |

FOREIGN PATENT DOCUMENTS

| CN | 1804595 B | 9/2010 |
| CN | 103163256 A | 6/2013 |
| WO | WO02066966 | 8/2002 |

OTHER PUBLICATIONS

Non-Final Office Action mailed Feb. 13, 2014 in co-pending U.S. Appl. No. 13/718,061, filed Dec. 18, 2012.
Non-Final Office Action mailed Sep. 24, 2014 in co-pending U.S. Appl. No. 13/718,061, filed Dec. 18, 2012.
Final Office Action mailed Nov. 18, 2015 in co-pending U.S. Appl. No. 13/718,061, filed Dec. 18, 2012.

* cited by examiner

*Primary Examiner* — Sam P Siefke

(57) ABSTRACT

A flame photometric detector (FPD) for use in a gas chromatography (GC) apparatus is described. The FPD has an emission block that is maintained in a first temperature range, and a transfer line that is maintained in a second temperature range that is greater than the first temperature range. The FPD is coupled to a light detector, such as a photomultiplier tube (PMT).

18 Claims, 4 Drawing Sheets

FLAME PHOTOMETRIC DETECTOR

BACKGROUND

Gas chromatography (GC) is used to analyze and detect the presence of many different substances in a gaseous or vaporized sample. Gas chromatography uses various types of detectors, depending on the specific element or compound sought to be detected. Different detectors are used to achieve selective and/or highly sensitive detection of specific elements or compounds in particular chromatographic analyses.

Typically, a flame photometric detector (FPD) is used to detect the presence of sulfur or phosphorus in a particular sample, or analyte. A flame photometric detector uses what is referred to as a chemiluminescent reaction where compounds containing sulfur or phosphorus encounter a hydrogen-rich flame. Chemiluminescence uses quantitative measurements of the optical emission from excited chemical species to determine analyte concentration. Chemiluminescence is typically emission from energized molecule species. When burned, or combusted, in such a flame, sulfur is transformed into an emitting species referred to as $S_2^*$ and phosphorus is transformed into an emitting species referred to as HPO*. The emission wavelength range for excited $S_2$ includes, among others, the region from 320-405 nanometers (nm) and the wavelength range for excited HPO includes, among others, the range from 510-530 nm. The molecular emissions impinge on a photomultiplier tube, which converts photons to an electrical signal to quantify the concentration of a particular excited species.

FPDs often incorporate a photomultiplier tube (PMT) to measure the number of photons and thus the intensity of light emitted from phosphorus and sulfur containing compounds, with wavelength selective filters disposed between the flame of the FPD and the PMT.

Generally, it is beneficial for FPD's to operate at temperatures equal to or exceeding the highest oven temperature reached during the analysis so that compounds eluting from the GC column do not condense before reaching the flame of the FPD. Such condensation would result in the measurement of inaccurate intensities of specific compound species, and ultimately in inaccurate measurements. Furthermore, there is a response temperature dependence that impacts parameters such as sensitivity and baseline noise of the FPD.

While it is desirable to operate the FPD at temperatures equal to or greater than the highest oven temperature reached during analysis, the PMT must be maintained at a comparatively low temperature to prevent the background noise of the PMT from impacting the accuracy of measurements. So, it is desirable to maintain the transfer line to the emission block of the FPD at a comparatively high temperature (e.g., 250° C.), while maintaining the PMT at a comparatively low temperature (e.g., 50° C.)

Additionally, there is demand to maintain the transfer line section of the FPD at even higher temperatures (e.g., 400° C.). Unfortunately, many current FPDs are limited to operation at approximately 250° C., above which mechanical failures can result. For example, seals between the transfer line and the detector block, between the flame igniter and the detector block, and around the window of the PMT can fail. The failure of these seals can initially impact the baseline noise of the PMT, thereby affecting accuracy of measurements.

What is needed, therefore, is an apparatus that overcomes at least the shortcomings of known structures described above.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

Figure 1:
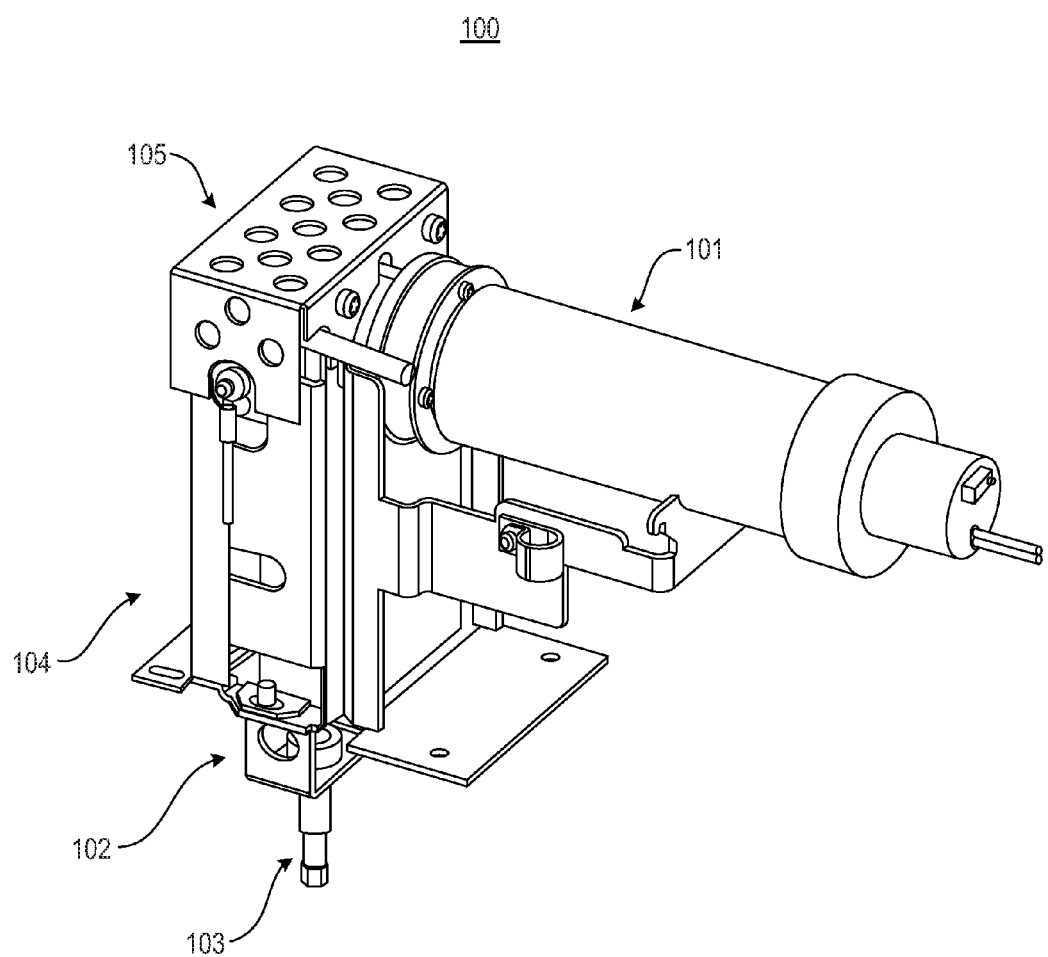
FIG. 1 shows a perspective view of an FPD comprising a PMT in accordance with a representative embodiment.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms 'a', 'an' and 'the' include both singular and plural referents, unless the context clearly dictates otherwise. Thus, for example, 'a device' includes one device and plural devices.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

As used in the specification and the appended claims and in addition to its ordinary meaning, the term 'approximately' means to within an acceptable limit or amount to one having ordinary skill in the art. For example, 'approximately the same' means that one of ordinary skill in the art would consider the items being compared to be the same.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials and methods that are within the purview of one of ordinary skill in the art may be used in accordance with the representative embodiments.

Representative embodiments are directed to an apparatus comprising an FPD and an FPD for use in GC applications. Generally, the apparatus comprises a transfer line having a heater block for controlling the temperature of a sample received from a GC separation column in a first temperature range. The transfer line is connected at one end to the sample input and at an opposing end is connected to a jet disposed in a cavity of an emission block. Notably, the transfer line is not in physical contact with the emission block. The emission block comprises a heater and temperature sensor to maintain the emission block in a second temperature range. A body tube is connected between a portion of the transfer line and the emission block. As described more fully below, the body tube has a comparatively high thermal impedance, and as a result, a significant temperature drop occurs over the length of the body tube. By contrast, the transfer line has a comparatively low thermal impedance so the temperature drop across the transfer line is comparatively small. Beneficially, the temperature of the sample can be maintained within the first temperature range, and the temperature of the emission block can be maintained within the second temperature range, that is significantly lower than the first temperature range.

FIG. 1 shows a perspective view of an FPD 100 comprising a PMT 101 in accordance with a representative embodiment. It is noted that the use of a PMT for light/photon detection is merely illustrative. Alternatively, other known types of optical detectors such as known photodiodes and phototransistors are contemplated. The FPD comprises a lower portion 102 comprising a column fitting 103. The column fitting 103 is connected to a column (not shown) and is disposed in the GC oven (not shown) of the GC apparatus (not shown) comprising the FPD 100. The column may end at the column fitting, or it may extend into the transfer line and end near the jet. The sample material exiting the column is referred to as the "effluent" and represents the output of the column. The FPD 100 comprises a transfer line section 104 that illustratively receives the effluent from the column fitting 103. Alternatively, the column may be configured to extend beyond the column fitting 103 and into the transfer line section 104 so that the sample exits the column near the opposing end of the transfer line section 104 (e.g., near the jet (not shown in FIG. 1)). As described more fully below, the transfer line section is configured to maintain the temperature of the sample within a transfer line (not shown in FIG. 1) to within a first temperature range, while not significantly impacting the temperature of other components of the FPD 100.

The FPD 100 also comprises an emission block 105 that comprises a jet (not shown in FIG. 1) and a cavity (not shown in FIG. 1). The various components of the FPD 100 are made of a selection of suitable materials. For example, much of the hardware is made of metal/metal alloy, such as stainless steel. Fittings are generally made of metal and alloys, and seals are generally made from synthetic materials, but can be made from metal/metal alloys as well. The materials used for the various components are generally within the purview of one of ordinary skill in the art, and are often not specifically recited herein to avoid obscuring the description of the representative embodiments.

As described more fully below, the emissions block 105 includes a jet (not shown in FIG. 1) to provide a flame (not shown). The sample is volatized in a hydrogen rich flame. Heating the sample in the hydrogen rich flame excites the molecules in the sample and if present, causes excited species of sulfur ($S_2$), or phosphorus to be formed from the effluent. Photon emission from relaxation from the excited state passes through an optical filter (not shown) and to the PMT 101, and then to a signal processor and data analyzer for signal analysis. Generally, the optical filter is a wavelength selective filter that allows photons from the desired emissions to pass to the PMT 101, while filtering out photoemissions from other species present in the effluent.

The optical filter may be as described in commonly owned U.S. Pat. No. 7,906,071 to Warchol, et al. The disclosure of U.S. Pat. No. 7,906,071 patent is specifically incorporated herein by reference.

As noted above, and as described more fully below, the emission block 105 is maintained in a second temperature range that is lower than the first temperature range. As such, the effluent in the transfer line in the transfer line section 104 is maintained in the desired first temperature range until it is burned in the flame, and the emission block 105 is maintained at the second temperature range that is lower than the first temperature range. Among other benefits, there is an unexpected advantage to keeping the emission block 105 at a lower temperature than the column temperature. Namely, because the lifetime of the excited species of sulfur is longer at lower temperatures, photon emission from this excited species is increased, and the sulfur response increases markedly at lower emission block temperature. Also the baseline level drops and the baseline noise decreases. These factors result in greatly reduced minimum detectable level (MDL) of sulfur compounds, illustratively by a factor of 2 or more. Moreover, maintaining the emission block in the second temperature range that is lower than first temperature range reduces inaccuracies and failure of the PMT due to operation at temperatures equal to the oven and column temperature.

Figure 2:
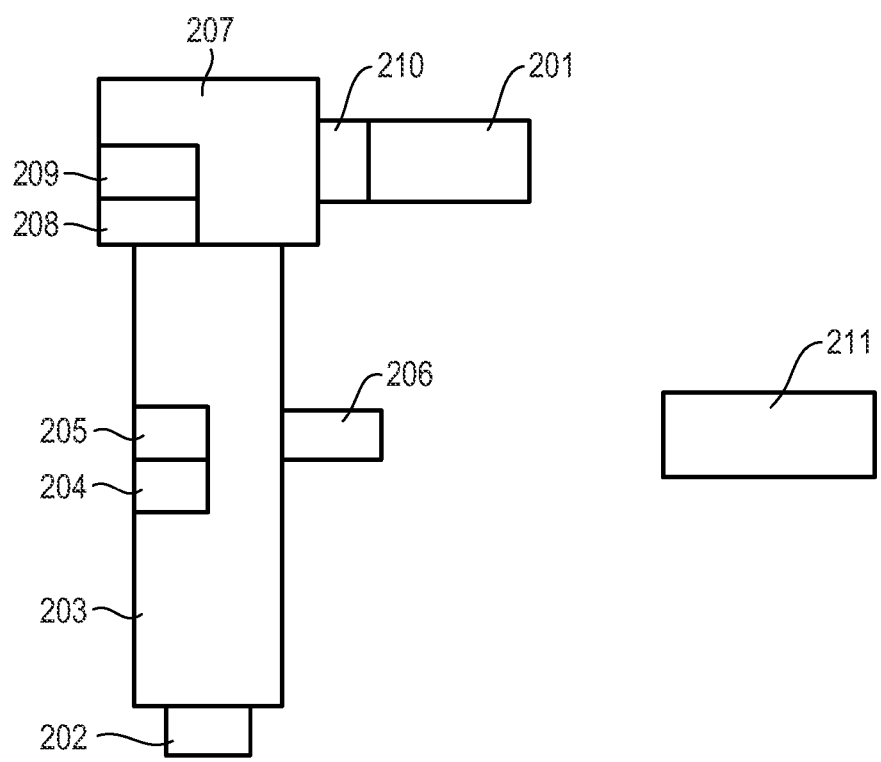
FIG. 2 shows simplified block diagram of an FPD comprising a PMT in accordance with a representative embodiment.

FIG. 2 shows a simplified block diagram of an FPD 200 comprising a PMT 201 in accordance with a representative embodiment. Many details of the FPD 200 are common to the FPD 100 described above, and are not repeated to avoid obscuring the presently described embodiment.

The FPD 200 comprises column fitting 202, which is disposed in the GC oven (not shown) of the GC apparatus (not shown) and is connected to a column of a GC apparatus (not shown). The column fitting 202 connects the column to a transfer line 203, which receives effluent either near the column fitting 202 (in the case of a packed column) or near the flame of the FPD (in the case of a capillary column). A first heater 204 and a first temperature sensor 205 are coupled to the transfer line 203 to maintain the temperature of the effluent to within a first temperature range. The first heater 204 is generally a known cylindrical cartridge heater such as a resistive heater, and is configured to fit around a portion of the transfer line 203. The first temperature sensor 205 is a known temperature sensor that periodically measures the temperature of the transfer line 203. Illustratively, the first temperature sensor 205 is a known platinum resistance thermometer (PRT) or thermocouple.

The FPD 200 comprises a gas line fitting 206 that includes an inlet for hydrogen for burning the effluent at the flame, and other inlets for other gases such as a purging gas or air useful during the operation of the FPD 200.

The FPD 200 also comprises an emission block 207. The emission block 207 comprises a jet (not shown in FIG. 2) and a cavity (not shown in FIG. 2) where burning of the effluent is effected. The emission block 207 also comprises a second heater 208 and a second temperature sensor 209. The second heater 208 is coupled to the emission block 207 to maintain the temperature of the emission block 207 within a second temperature range. The second heater 208 is generally a known cartridge heater such as a resistive heater (e.g., a known wire heated by passing current therethrough), in order to meet power requirements to heat the emission block. The second heater 208 is disposed at a selected portion of the emission block 207 to maintain the temperature as desired. The second temperature sensor 209 is a known temperature sensor that periodically measures the temperature of the emission block 207. Illustratively, the second temperature sensor 209 is a known platinum resistance thermometer (PRT) or thermocouple.

It is noted that in certain applications, the second heater 208 and second temperature sensor 209 are optional. Notably, in the detection of sulfur compounds (S-mode operation) the response of the FPD 200 is a function of the temperature of the emission block 207. As such, the second heater 208 is useful in maintaining the temperature in a desired temperature range. However, in the detection of phosphorus compounds (P-mode operation), it is possible that power received through the body tube (discussed below) could suffice for heating the emission block. Notably, in such an embodiment, insulation around the emission block would be useful. As such, in some embodiments, the second heater 208 and the second temperature sensor 209 could be foregone.

As described more fully below, the temperature of the emission block 207 is maintained at a comparatively low temperature, whereas the transfer line 203 is maintained at a comparatively high temperature. Generally, the emission block 207 is maintained at a temperature above the boiling point of water to prevent condensation within the emission block. Preventing condensation avoids water droplets from interfering with or extinguishing the flame of the FPD 200. Moreover, preventing condensation avoids "fogging" the window of the PMT and "spotting" or water marks on the walls of the emission block, which could reduce light normally reflected into the PMT. Thereby certain inaccuracies in spectral data can be mitigated or avoided. However, the emission block 207 is maintained at a temperature low enough so that damage to certain components (e.g., seals and the PMT 201) of the FPD 200 and undesirable levels of background noise in the PMT output are avoided. Illustratively, the second heater 208 maintains the emission block 207 in a range of approximately 125° C. to approximately 175° C.

The first heater 204 maintains the transfer line 203 at a temperature substantially equal to or even greater than the column temperature and the oven temperature of the GC apparatus to substantially prevent the condensation of the sample before it reaches the flame of the jet within the emission block 207. Illustratively, the first heater 204 maintains the temperature of the transfer line 203 in a range of approximately 200° C. to approximately 400° C.

An optical filter 210 is provided between the emission block and the PMT 201. The optical filter 210 is a wavelength selective filter that allows photons from the desired emissions to pass to the PMT 201, while filtering out photoemissions from other species present in the effluent.

The FPD 200 is connected to a controller 211, which is connected to a power supply (not shown), a signal amplifier (not shown) and a signal analog-to-digital converter (ADC) (not shown) to effect certain functions of the FPD 200. The controller 211 may be a controller of the GC apparatus (not shown), or may be a dedicated controller configured to perform certain functions associated with the FPD 200. The controller 211 may be a processor, such as a computer processor or a digital signal processor (DSP), one or more application specific integrated circuits (ASICs), one or more field-programmable gate arrays (FPGAs), or combinations thereof, using software, firmware, hard-wired logic circuits, or combinations thereof. When using a computer processor and/or a DSP, for example, a memory may be included for storing executable software/firmware and/or executable code that allows it to perform the various functions. The memory may be a non-transitory computer readable medium, and may include any number, type and combination of random access memory (RAM) and non-volatile memory (e.g., read-only memory (ROM)), for example.

Among other functions, the controller 211 is configured to receive temperature data from the first temperature sensor 205 and the second temperature sensor 209. Based on these temperature data the controller is configured make adjustments to the output of the first heater 204, or to the output of the second heater 208, or both, to maintain the transfer line 203 in the first temperature range and to maintain the emission block in the second temperature range. The controller 211 may be configured to effect other functions, such as the control of gas flow of gases to the various inlets of the gas line fitting 206. Additionally, the controller 211 functions as a signal processor for the PMT 201, and can communicate data to an external device (e.g., a computer) for analysis of the data. At minimum the PMT signal output is provided to the controller 211, but usually a suitable analog signal (amplified, filtered) would be provided. More common is a full-range digital signal with user selectable data rates, and a possible full system that outputs component concentrations in some way. The signal processing effected at the controller 211 typically involves digitizing, filtering, and then integrating and identifying peaks that result from sample component elution. The architecture for this can be varied. Illustratively, one or more dedicated processors are provided in the GC system, which then transmits digitized data to an external computer where peaks are integrated and identified, but other architectures can be used.

Figure 3:
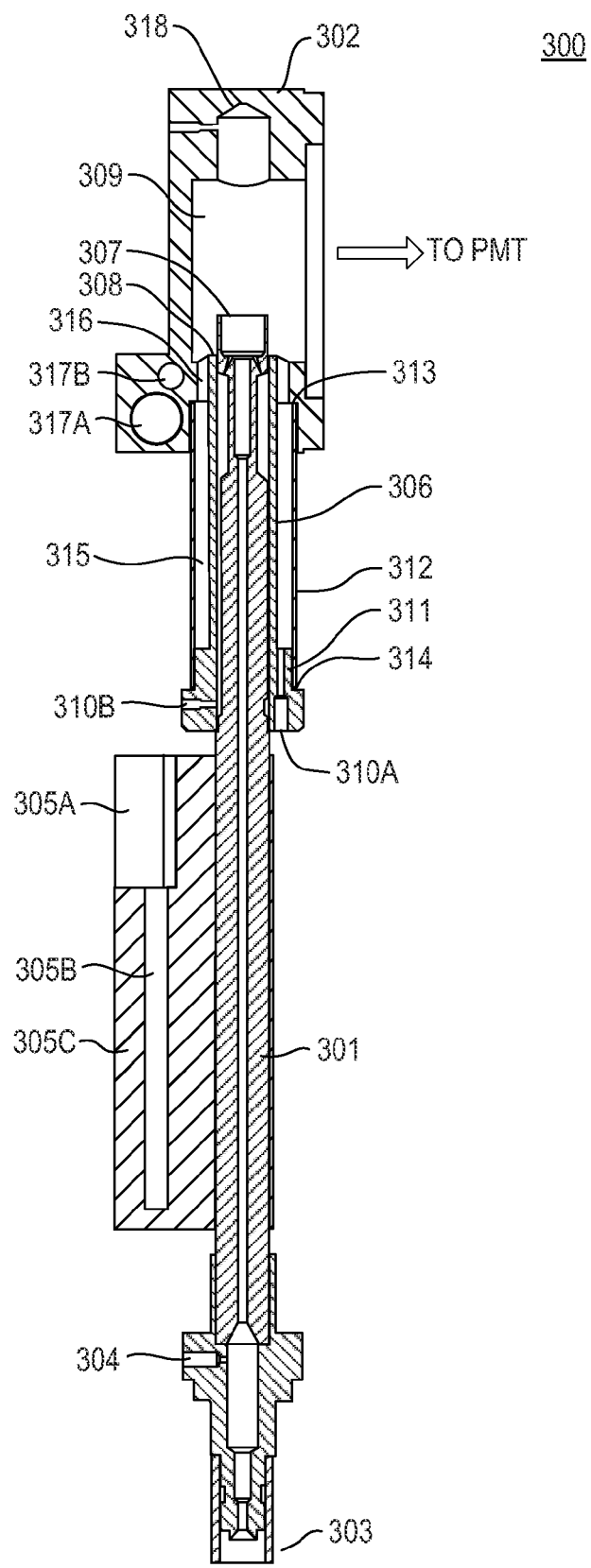
FIG. 3 is a cross-sectional view of an FPD in accordance with a representative embodiment.

FIG. 3 is a cross-sectional view of a transfer line 301 connected between a column of a GC apparatus (not shown) and an emission block 302 of an FPD 300 in accordance with a representative embodiment. Many details of the FPD 300 are common to the FPDs 100, 200 described above, and are not repeated to avoid obscuring the presently described embodiment.

The FPD 300 comprises a column fitting 303 that connects the transfer line 301 to the column of the GC apparatus. As noted above, the column fitting 303 is disposed in the GC oven (not shown) of the GC apparatus (not shown). A first gas fitting 304 is included for providing hydrogen gas and so-called make-up gas (e.g., $N_2$) for use in the FPD 300.

A temperature sensor 305A and a transfer line heater 305B are provided on a transfer line block 305C, which is illustratively aluminum or another suitable thermal conductor. The transfer line block 305C is disposed around at least a portion of the transfer line 301 for maintaining the temperature of the transfer line 301 (and the effluent therein) to within a desired temperature range. As noted above, the transfer line heater 305B is generally a known cartridge heater such as a resistive heater such as a known wire heated by passing current therethrough. The temperature sensor 305A is a known temperature sensor that periodically measures the temperature of the transfer line block 305C.

As noted above, the transfer line 301 is maintained at a temperature substantially equal or even greater than the column temperature and the oven temperature of the GC apparatus to substantially prevent the condensation of the sample before it reaches the flame of the jet within the emission block 302. Illustratively, the transfer line heater 305 maintains the temperature of the transfer line 301 in a range of approximately 200° C. to approximately 400° C.

The FPD 300 also comprises a jet housing 306 with a jet 307 provided at one end (the "top end") 308 thereof and inside a cavity 309 of the emission block 302. The FPD 300 comprises a gas inlet 310A and a gas inlet 310B at a second end (the "bottom end") 311 of the jet housing 306. Purge gas is introduced through gas inlet 310A and air is introduced through gas inlet 310B. The burning of the effluent from the transfer line 301 is effected by the jet 307 in the cavity 309, and spectra therefrom are provided to the PMT (not shown in FIG. 3).

A body tube 312 is disposed around the portion of the transfer line 301 that is disposed in the jet housing 306. The body tube 312 is connected at a first end 313 to the emission block 302 and at a second end 314 at the second end 311 of the jet housing 306. Illustratively, the first end 313 of the body tube 312 is brazed to the emission block 302 and the second end 314 of the body tube 312 is brazed at the second end 311 by a known technique. The brazing of the body tube 312 at the first end 313 to the emission block 302 and at the second end 314 to the second end 311 of the jet housing 306 provides a good thermal contact at both ends of the body tube 312. As described more fully below, this good thermal contact is useful in maintaining the emission block 302 at the second temperature range and the transfer line 301 at the first temperature range, which is greater than the second temperature range.

The body tube 312 is illustratively a hollow cylinder made of a suitable metal/metal alloy. For example, the body tube 312 may be stainless steel suitable for brazing. Moreover, the walls of the body tube 312 are comparatively thin to foster (thermal) power dissipation and a comparatively large temperature change between the first end 313 and the second end 314 of the body tube 312. Illustratively, the walls of the body tube 312 have a thickness of approximately 0.381 mm to approximately 0.508 mm. As described more fully below, this allows the transfer line 301 to be maintained in a first temperature range and the emission block to be maintained in the second temperature range that is lower than the first temperature range. Beneficially, the effluent is maintained to within a desired temperature range from the column through the transfer line 301 and to the jet 307; and the emission block 302 is maintained at a suitable temperature to prevent failure of seals, or damage to the PMT, or both.

A first gap 315 is provided between the body tube 312 and the jet housing 306. Moreover, a second gap 316 is provided between the jet housing 306 and the emission block 302. The first gap 315 provides suitable thermal isolation between the transfer line 301 in the jet housing 306 and the body tube 312, and the second gap 316 provides suitable thermal isolation between the transfer line 301 and the emission block 302. As a result, the transfer line 301 has a comparatively low thermal impedance, and the loss of thermal power along this length of the transfer line 301 is comparatively small. Accordingly, the temperature drop along the length of the transfer line 301 between the bottom end 311 of the jet housing 306 and the top end 308 of the jet housing 306 is comparatively small. As such, the temperature of the transfer line 301 disposed in the jet housing 306 is maintained to a desired temperature range through conduction from transfer line heater 305 and heat from the flame of the jet 307. Beneficially, the temperature of the transfer line 301 and the effluent therein can be maintained to within a desired temperature range between the column fitting 303 and the jet 307.

As depicted in FIG. 3, an emission block heater 317A and a temperature sensor 317B are provided adjacent to the emission block 312. As noted above, the emission block heater 317A is generally a known cartridge heater such as a resistive heater such as a known wire heated by passing current therethrough, in order to meet power requirements to heat the emission block 302. The emission block heater 317A is disposed at a selected position of the emission block 302 to maintain the temperature as desired. The temperature sensor 317B is a known temperature sensor that periodically measures the temperature of the emission block 302.

As noted above, in the S-mode operation the response of the FPD 300 is a function of the temperature of the emission block 207. As such, the emission block heater 317A is useful in maintaining the temperature in a desired temperature range. However, in the P-mode operation, it is possible that power received through the body tube 312 could suffice for heating the emission block 302. Notably, in such an embodiment, insulation around the emission block 302 would be useful. As such, in some embodiments, the emission block heater 317A and the temperature sensor 317B could be foregone.

The heat transfer through a thin metal tube (e.g., body tube 312) is axial along the length of the tube with little power dissipated radially inwardly or outwardly. As such, the body tube 312 has a comparatively high thermal impedance. This allows for a significant change in temperature along the length of the body tube 312 between the first end 313 and the second end 314 of the body tube 312. Moreover, and as noted above, the body tube 312 is brazed to the emission block 302 at its first end 313, and is brazed to the jet housing 306 at its second end 314 (at the bottom end 311 of the jet housing 306). Beneficially, because of the brazing of the body tube 312 to the emission block 302 and to the jet housing at the bottom end 311, and because of the temperature difference between the first and second ends 313, 314 of the body tube, the emission block 302 can be maintained in a first temperature range, and the transfer line 301 in the jet housing 306 is maintained in a second temperature range that is greater than the first temperature range.

In a representative embodiment, a purging gas (e.g., $N_2$) is provided through the second gap 316. In addition to providing thermal isolation between the transfer line 301 in the jet housing 306 and the body tube 312, this purging gas beneficially removes and prevents effluent from the seeping into the first gap 315, and is emitted along with other gases through a vent 318. As should be appreciated by one of ordinary skill in the art, without the purging gas in the first gap 315, a dead volume can exist. Ultimately, effluent in the dead volume can be excited by the flame of the jet 307 resulting in undesirable "tails" in the emission spectral response of the GC apparatus that comprises the FPD. By the present teachings these "tails" can be substantially avoided.

Figure 4:
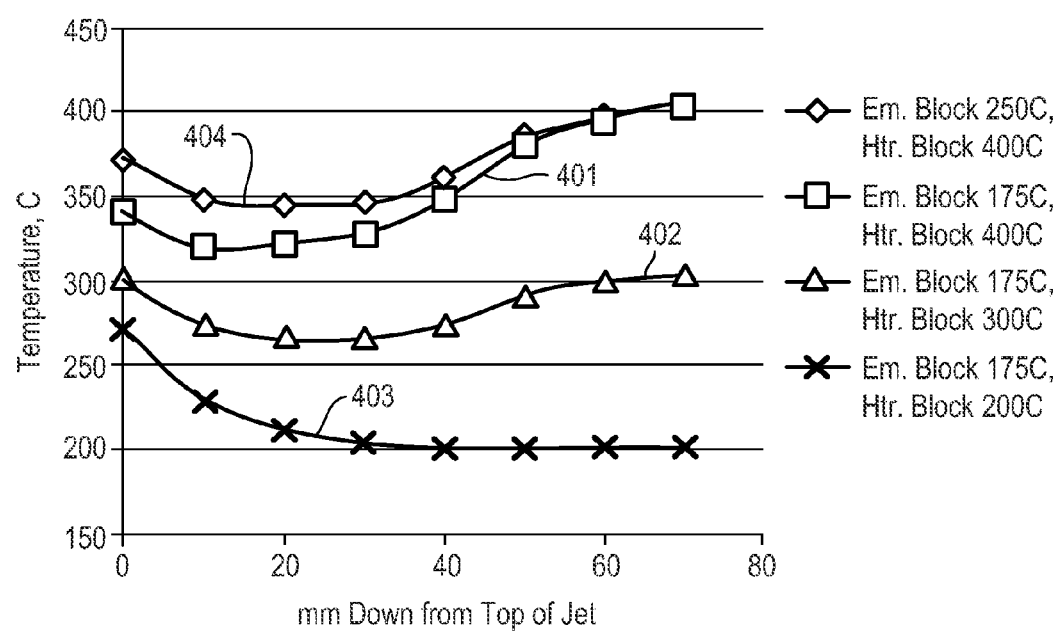
FIG. 4 shows a graph of distance from a jet (flame source) versus temperature for different combinations of emission block temperature and heater block temperature for FPDs in accordance with a representative embodiment.

FIG. 4 shows a graph of distance from a jet (e.g., jet 307) versus temperature inside the transfer line for different combinations of emission block 302 temperature and heater block 305C temperature for FPDs in accordance with a representative embodiment. The unit along the x-axis is millimeters and the unit along the y-axis is ° C. Turning to FIG. 3, the jet 307 is located at 0 (zero) mm and the vertical distance downward (towards the column fitting 303) is presented in the gradation to 130 mm depicted. Curve 401 depicts the temperature as a function of distance with the heater block maintained at 400° C.; curve 402 depicts the temperature as a function of distance with the heater block maintained at 300° C.; and curve 403 depicts the temperature as a function of distance with the heater block maintained at 200° C. The emission block 302 is maintained at 175° C. for curves 401, 402 and 403. Curve 404 depicts the temperature as a function of distance with the heater block maintained at 400° C. and the emission block 302 maintained at 250° C. The flame is burning for all data. Notably, the jet and the region approximately 30 mm from the jet are heated by the flame. As can be appreciated, the temperature of the transfer line is substantially maintained along its length from the jet to be reasonably close to the heater block temperature.

In view of this disclosure it is noted that the methods and devices can be implemented in keeping with the present teachings. Further, the various components, materials, structures and parameters are included by way of illustration and example only and not in any limiting sense. In view of this disclosure, the present teachings can be implemented in other applications and components, materials, structures and equipment needed to implement these applications can be determined, while remaining within the scope of the appended claims.

The invention claimed is:

1. An apparatus for receiving a gas chromatography column, the apparatus comprising:
   a transfer line having a first end and a second end opposing the first end;
   a heater block disposed around a first portion of the transfer line, the heater block comprising a heater configured to maintain the first portion of the transfer line at a first temperature range;
   an emission block configured to receive the second end of the transfer line; and
   a body tube substantially surrounding a second portion of the transfer line such that a gap is provided between the body tube and the second portion of the transfer line, the body tube mechanically and thermally coupled to the emission block, wherein the emission block and the body tube are maintained at a second temperature range that is lower than the first temperature range, and the second portion of the transfer line is maintained at the first temperature range.

2. An apparatus as claimed in claim 1, wherein the heater is a first heater and the emission block comprises a second heater configured to maintain the emission block at the second temperature range.

3. An apparatus as claimed in claim 2, further comprising a controller configured to maintain the second heater so that the emission block is maintained at the second temperature range.

4. An apparatus as claimed in claim 1, wherein the body tube is brazed to the emission block.

5. An apparatus as claimed in claim 1, further comprising a jet housing disposed around the second portion of the transfer line, wherein the jet housing is brazed to the transfer line.

6. An apparatus as claimed in claim 5, wherein the body tube is brazed to the emission block at a first end of the body tube, and the body tube is brazed to the jet housing at a second end of the body tube.

7. An apparatus as claimed in claim 5, further comprising a space between the jet housing and the transfer line, wherein the space is configured to receive a gas.

8. An apparatus as claimed in claim 5, further comprising a space between the jet housing and the body tube.

9. An apparatus as claimed in claim 1, wherein the body tube is made of metal or a metal alloy.

10. A flame photometric detector (FPD), comprising:
    a transfer line having a first end and a second opposing end;
    a heater block disposed around a first portion of the transfer line, the heater block comprising a heater configured to maintain the first portion of the transfer line at a first temperature range;
    an emission block configured to receive the second opposing end of the transfer line;
    a body tube substantially surrounding a second portion of the transfer line such that a gap is provided between the body tube and the second portion of the transfer line, the body tube mechanically and thermally coupled to the emission block; and
    a photodetector coupled to the emission block for receiving light from the emission block, wherein the emission block and the body tube are maintained at a second temperature range that is lower than the first temperature range and the second portion of the transfer line is maintained at the first temperature range.

11. An FPD as claimed in claim 10, wherein the heater is a first heater and the emission block comprises a second heater configured to maintain the emission block at the second temperature range.

12. An FPD as claimed in claim 11, further comprising a controller configured to maintain the second heater so that the emission block is maintained at the second temperature range.

13. An FPD as claimed in claim 10, wherein the body tube is brazed to the emission block.

14. An FPD as claimed in claim 10, further comprising a jet housing disposed around the second portion of the transfer line, wherein the jet housing is brazed to the transfer line.

15. An FPD as claimed in claim 14, wherein the body tube is brazed to the emission block at a first end of the body tube, and the body tube is brazed to the jet housing at a second end of the body tube.

16. An FPD as claimed in claim 14, further comprising a space between the jet housing and the transfer line, wherein the space is configured to receive a gas.

17. An FPD as claimed in claim 14, further comprising a space between the jet housing and the body tube.

18. An FPD as claimed in claim 10, wherein the body tube is made of metal or a metal alloy.

* * * * *